United States Patent [19]

Daubie et al.

[11] Patent Number: 5,484,921

[45] Date of Patent: Jan. 16, 1996

[54] PROCESS FOR PREPARING BENZO[B]NAPHTHYRIDINES

[75] Inventors: Christophe Daubie; Jean-Jacques Legrand, both of Paris, France; Clive Pemberton, Romfold, Great Britain

[73] Assignee: Laboratoire Roger Bellon, Neuilly-sur-Seine, France

[21] Appl. No.: 211,443

[22] PCT Filed: Oct. 8, 1992

[86] PCT No.: PCT/FR92/00937

§ 371 Date: Apr. 8, 1994

§ 102(e) Date: Apr. 8, 1994

[87] PCT Pub. No.: WO93/07145

PCT Pub. Date: Apr. 15, 1993

[30] Foreign Application Priority Data

Oct. 10, 1991 [FR] France .................. 91 12479

[51] Int. Cl.⁶ .................. C07D 401/12; C07D 471/04; C07D 417/12

[52] U.S. Cl. .................. 544/361; 546/81; 544/55; 544/60; 544/96; 544/126; 544/238; 544/333

[58] Field of Search .................. 546/81; 544/55, 544/60, 96, 126, 238, 333, 361

[56] References Cited

PUBLICATIONS

Chemical Abstracts, vol. 114(7) Abst. No. 114:62082J, Feb. 18, 1991.
Chemical Abstracts, vol. 114(15) Abst. No. 114:143,393p, Apr. 15, 1991.
Journal of Medicinal Chemistry, vol. 18, No. 10, 1975, pp. 1038–1041 A. A. Santilli "Synthesis and antibacterial evaluation of 1,2,3 4–tetrahydro–4–oxo–1, 8–naphthyridine–3–carboxylic acid esters, carbonitriles, and carboxamides".

Primary Examiner—Alan L. Rotman
Attorney, Agent, or Firm—Finnegan, Henderson, Farabow, Garrett & Dunner

[57] ABSTRACT

This invention relates to a method for the preparation of benzo[b]naphthyridines having the general formula (I)

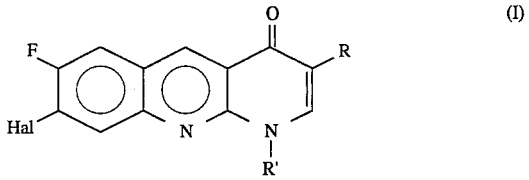

comprising:
1) condensation of an amine having the formula R'—NH—CH$_2$—CH$_2$—R" with a chlorofluoroquinoline of formula (II)

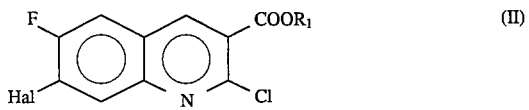

2) cyclization of the obtained fluoroquinoline of formula (IV)

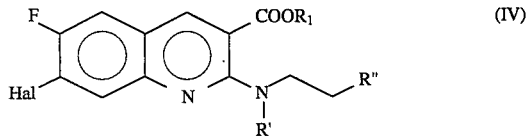

and;
3) oxidation of tetrahydro-1,2,3,4benzo[b]naphthyridine-1,8 of formula (V)

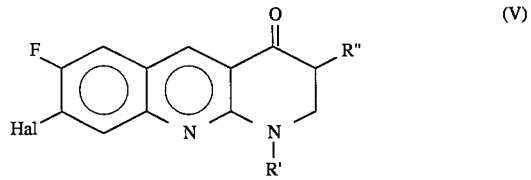

is effected, and then, optionally, the ester obtained is transformed into an acid and optionally into a salt.

2 Claims, No Drawings

PROCESS FOR PREPARING BENZO[B] NAPHTHYRIDINES

FIELD OF THE INVENTION

This application is a 371 of FR 9400937 filed Oct. 8, 1992.

The present invention relates to a new process for preparing benzo[b]naphthyridines of general formula:

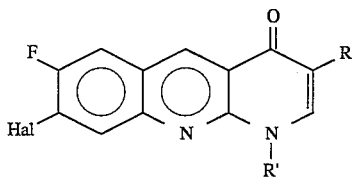

in which R is a carboxyl, alkyloxycarbonyl, cyano, carbamoyl, alkylcarbamoyl, benzylcarbamoyl or hydroxyethylcarbamoyl radical or a dialkylaminoethylcarbamoyl or dialkylcarbamoyl radical in which the alkyl portions, with the nitrogen atom to which they are attached, can optionally form a 5- or 6-membered heterocycle optionally containing another hetero atom chosen from oxygen, sulphur and nitrogen and optionally substituted on the nitrogen with an alkyl radical, R' is hydrogen atom or an alkyl, fluoroalkyl, carboxyalkyl, cycloalkyl (containing 3 to 6 carbon atoms), fluorophenyl, difluorophenyl, alkyloxy or alkylamino radical and Hal is a halogen atom, as well as their salts where they exist.

BACKGROUND OF THE INVENTION

The benzo[b]naphthyridines of general formula (I), as well as their preparation and their use for the preparation of antibacterial agents, have been described in U.S. Pat. Nos. 4,970,213 and 4,990,515.

DESCRIPTION OF THE INVENTION

It has been found that the benzo[b]naphthyridine derivatives of general formula (I) may be prepared from a quinoline derivative of general formula:

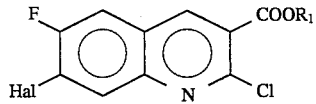

in which Hal is defined as above and $R_1$ is a hydrogen atom or an alkyl radical, by performing the following operations:

1) condensation of an amine of general formula:

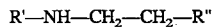

R'—NH—CH$_2$—CH$_2$—R"         (III)

in which R' is defined as before and R" is an alkyloxycarbonyl, cyano, carbamoyl, alkylcarbamoyl, benzylcarbamoyl or hydroxyethylcarbamoyl radical or a dialkylaminoethylcarbamoyl or dialkylcarbamoyl radical in which the alkyl portions, with the nitrogen atom to which they are attached, can optionally form a 5- or 6-membered heterocycle optionally containing another hetero atom chosen from oxygen, sulphur and nitrogen and optionally substituted on the nitrogen with an alkyl radical, with a chlorofluoroquinoline of general formula (II) in which $R_1$ is an alkyl radical, 2) cyclization of the fluoroquinoline thereby obtained, of general formula:

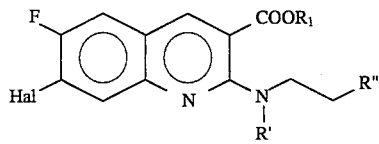

in which R', R" and Hal are defined as before and $R_1$ is defined as above in 1), 3) oxidation of the 1,2,3,4-tetrahydrobenzo[b][1,8]naphthyridine of general formula:

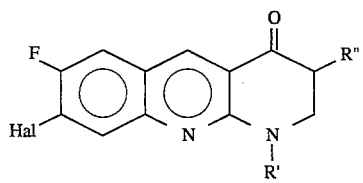

in which Hal, R' and R" are defined as before, and then, optionally, conversion of the ester of general formula (I) thereby obtained to an acid for which R is a carboxyl radical and, optionally, conversion of the acid obtained to a salt.

The new process according to the present invention is especially advantageous on account of the fact that it enables improved yields to be obtained and also on account of the fact that it avoids the involvement of unstable intermediate products.

In the general formulae mentioned above or to be mentioned below, it is understood that the alkyl radicals are unbranched or branched and contain 1 to 4 carbon atoms. Moreover, the symbol Hal is advantageously chosen from chlorine or fluorine.

The condensation of the β-amino ester of general formula (III) is performed on the quinoline derivative of general formula (II) in which, where appropriate, the acid function is protected in the ester state. The reaction is performed in a basic medium, in an organic solvent such as an aromatic hydrocarbon (e.g. toluene), an amide (e.g. dimethylformamide, N-methylpyrrolidone), an ether (e.g. tetrahydrofuran), a sulphoxide (e.g. dimethyl sulphoxide), a chlorinated solvent (e.g. dichloromethane, dichloroethane, chlorobenzene) or an alcohol at a temperature of between −10° and 120° C.

As an example, the bases used may be chosen from alkali metal carbonates (sodium or potassium carbonate) alcoholates and an alkali metal hydride (sodium hydride).

It is understood that, in the option where the symbol R' represents a carboxyalkyl radical, the latter is protected prior to the reaction. Removal of the protective radical is preferably performed after the oxidation step 3). Protection and liberation of the acid function are performed according to customary methods which have no adverse effect on the remainder of the molecule; in particular, according to the methods mentioned in the references below.

The cyclization reaction of the product of general formula (IV) is performed in a basic medium. It is advantageous to work at a temperature of between −70° and 120° C., and preferably between −30° and 120° C., in the presence of a base such as an alcoholate (e.g. sodium ethylate, sodium methylate, potassium t-butylate), an alkali metal hydride (e.g. sodium hydride) or alternatively an alkali metal hydroxide, working under phase transfer conditions. It is advantageous to work in a polar aprotic solvent (e.g. dimethylformamide, tetrahydrofuran) or in an alcohol (e.g.

ethanol, methanol), in a glyme or in a glycol (e.g. ethylene glycol). When the reaction is performed under phase transfer conditions, it is advantageous to work in a chlorinated solvent such as methylene chloride, the base being dissolved in the aqueous phase.

The oxidation is performed with hydrogen peroxide, optionally in the presence of potassium iodide, in an organic solvent such as an alcohol (e.g. ethanol), at a temperature of between 0° and 120° C. It is also possible to work in a two-phase medium in a water/chlorinated solvent (dichloromethane, dichloroethane, etc.) mixture.

The quinoline derivative of general formula (II) may be obtained according to the method described in U.S. Pat. No. 4,970,213, optionally followed by esterification of the product obtained according to the customary methods.

The quinoline derivative of general formula (II) may also be obtained by chlorination of a quinoline derivative of general formula:

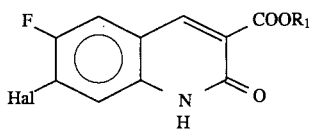
(VI)

in which $R_1$ and Hal are defined as before.

The chlorination is performed by means of known chlorinating agents which have no adverse effect on the remainder of the molecule. In particular, the chlorination is performed by the action of phosphoryl chloride, sulfuryl chloride or phosphorus pentachloride at a temperature of between 0° and 150° C. It is understood that, when the reaction is performed using a quinoline derivative of general formula (VI) for which $R_1$ is a hydrogen atom, it is necessary to protect the acid function beforehand. When it is desired to obtain the acid of general formula (II) in which $R_1$ is a hydrogen atom, hydrolysis of the ester obtained is performed by any known method which has no adverse effect on the remainder of the molecule. Protection of the acid function and removal of the protective radical may be carried out with any group and by any compatible method whose use and removal have no adverse effect on the remainder of the molecule. In particular, the methods employed are those described by T. W. GREENE, Protective Groups in Organic Chemistry, A. Wiley Interscience Publication (1981), or by McOMIE, Protective Groups in Organic Chemistry, Plenum Press (1973).

The quinoline derivative of general formula (VI) may be prepared by cyclization in an acid medium of a nitro derivative of general formula:

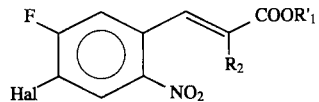
(VII)

in which Hal is defined as before, $R'_1$ is defined like $R_1$ with the exception of representing a hydrogen atom and $R_2$ is defined like $R'_1$ or represents a carbamoyl or cyano radical, optionally followed by liberation of the acid function if it is desired to obtain a quinoline derivative for which $R_1$ is a hydrogen atom.

The treatment in an acid medium is formed in the presence of iron, at a temperature of between 0° and 130° C., by means of any organic or inorganic acid which has no adverse effect on the remainder of the molecule. As an example, the reaction is performed using acetic acid or formic acid; it is also possible to perform it using dilute hydrochloric acid or dilute sulphuric acid in an aqueous-alcoholic medium. It is, of course, understood that the choice of acid is dependent on the product expected. In the case where it is desired to obtain the acid of general formula (VI), it is advantageous to work in a stronger acid, under conditions in which hydrolysis of the ester takes place simultaneously; it can also be advantageous to perform the reaction using the product of general formula (VII) for which $R_2$ is cyano. It is, of course, understood that, in cases where the ester has been obtained and where it is desired to obtain the acid of general formula (VI) for which $R_1$ is a hydrogen atom, the hydrolysis of the ester may also be carried out after the cyclization reaction, by any known method for obtaining an acid from an ester without affecting the remainder of the molecule.

When appropriate, the hydrolysis of the ester is performed in an acid medium, e.g. in the presence of hydrochloric acid, sulphuric acid or methanesulphonic acid. It may also be performed in a basic aqueous-alcoholic medium (e.g. sodium hydroxide, potassium hydroxide).

The nitro derivative of general formula (VII) may be prepared by the action of a malonic acid derivative of general formula:

$$R_2-CH-COOR'_1 \quad (VIII)$$

in which $R'_1$ and $R_2$ are defined as before, on a nitrobenzaldehyde derivative of general formula:

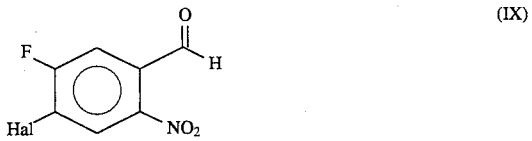
(IX)

in which Hal is defined as before.

The reaction is generally performed in a basic medium [e.g. in the presence of an alkali metal bicarbonate (sodium bicarbonate), a hydride (sodium hydride) or an alcoholate [lacuna] at a temperature of between 0° and 150° C., in an organic solvent such as an anhydride (e.g. acetic anhydride) or such as an amide (e.g. dimethylformamide, N-methylpyrrolidone), working in the presence of molecular sieves or any other dehydrating agent, or alternatively in a mixture of solvents such as a polar aprotic solvent/acetic anhydride (e.g. dimethylformamide/acetic anhydride, N-methylpyrrolidone/acetic anhydride) mixture. It is also possible to work in a two-phase medium. It is not essential to isolate the product of general formula (VII) in order to use it in the following reaction.

The fluoronitrobenzaldehyde of general formula (IX) is obtained by nitration of the fluorobenzaldehyde of general formula:

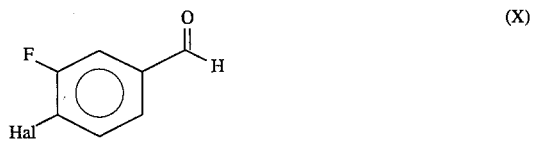
(X)

in which Hal is defined as before.

The reaction is advantageously performed with concentrated nitric acid in the form of a nitric acid/sulphuric acid mixture or of a nitric acid/acetic acid mixture at a temperature of between 0° and 90° C.

4-Chloro-3-fluorobenzaldehyde may be prepared according to the method described in European Application EP 289,942.

According to the invention, the benzonaphthyridine derivatives of general formula (I) in which R is a cyano, carbamoyl, alkylcarbamoyl, benzylcarbamoyl or hydroxyethylcarbamoyl radical or a dialkylaminoethylcarbamoyl or dialkylcarbamoyl radical in which the alkyl portions, with the nitrogen atom to which they are attached, can optionally form a 5- or 6-membered heterocycle optionally containing another hetero atom chosen from oxygen, sulphur and nitrogen and optionally substituted on the nitrogen with an alkyl radical are new products.

The benzo[b]naphthyridine derivatives of general formula (I) obtained according to the process of the present invention are particularly advantageous on account of the fact that they lead to a family of especially active antibacterial agents defined by the general formula:

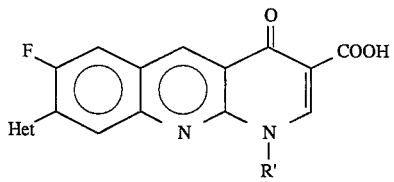

(XI)

in which either R' (which represents an alkyl or fluoroalkyl radical, a cycloalkyl radical containing 3 to 6 carbon atoms or an alkyloxy or alkylamino radical) and Het (which is a nitrogenous heterocyclic radical) are as defined for the substituents at positions 1 and 8 in European Application EP 431,991 and U.S. Pat. No. 5,004,745, or R' is defined as before for the general formula (I) and et is a substituted 1-azetidinyl radical (substituted at position 3 with a radical $R_2$ which can be a hydrogen atom or a hydroxyl or amino radical or an alkylamino radical in which the alkyl portion is optionally substituted with an amino or hydroxyl radical, or can represent a dialkylamino radical in which the alkyl portions, with the nitrogen atom to which they are attached, can optionally form a 5- or 6-membered heterocycle optionally containing another hetero atom chosen from nitrogen, oxygen and sulphur, or can represent a (3- to 6-membered cycloalkyl)amino radical or an alkanoylamino, N-alkyl-N-alkanoylamino or aminoalkylphenylamino radical, and substituted at positions 2 and 3 with identical or different radicals $R_3$ and $R_4$ which represent hydrogen atoms, alkyl radicals, alkenyl radicals containing 2 to 4 carbon atoms, phenyl radicals or phenyl radicals substituted with a halogen atom or with an alkyl, alkyloxy, hydroxyl, nitro, amino, alkylamino, dialkylamino or haloalkyl radical, or alternatively substituted at position 2 with radicals $R_3$ and $R_4$ which represent alkyl radicals), the alkyl and alkanoyl radicals being unbranched or branched and containing 1 to 4 carbon atoms.

The benzo[b][1,8]naphthyridine derivatives of general formula (XI) are obtained by condensing the heterocycle Het with the benzo[b]naphthyridine of general formula (I), working according to the methods described in European Application EP 431,991 and Patent U.S. Pat. No. 5,004,745 or by methods analogous thereto, and then, where appropriate, converting the ester, amide or nitrile obtained to an acid of general formula (XI). The activities of the benzonaphthyridine derivatives of general formula (XI) have been described in the European Application and the US Patent cited above. The benzonaphthyridine derivatives of general formula (XI) for which et is an azetidinyl radical also possess antibacterial properties. They manifest exceptional activity in vitro and in vivo against Gram-positive microorganisms and also against Gram-negative microorganisms. In vitro, they are active at a concentration of between 0.06 and 4 µg/cc against Staphylococcus aureus IP 8203, and at a concentration of between 0.25 and 20 µg/cc against Escherichia coli strain NIHJ JC2. In vivo, they are active against experimental Staphylococcus aureus IP 8203 infections of mice at oral doses of between 10 and 200 mg/kg.

The benzo[b]naphthyridine derivatives of general formula (I) obtained according to the process of the present invention can be optionally purified by physical methods such as crystallization or chromatography.

When the radical R is a hydrogen atom, the benzo[b]naphthyridine derivatives of general formula (I) may be converted to metal salts or to addition salts with nitrogenous bases according to methods known per se. These salts may be obtained by the action of a metal-containing base (containing, e.g., an alkaline or alkaline earth metal), ammonia or an amine on a product according to the invention in a suitable solvent such as an alcohol, an ether or water, or by an exchange reaction with a salt of an organic acid. The salt formed precipitates after concentration, where appropriate, of its solution; it is separated by filtration, decantation or lyophilization.

As examples of salts, there may be mentioned the salts with alkali metals (sodium, potassium, lithium) or with alkaline earth metals (magnesium, calcium), the ammonium salt, salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine, dibenzylamine) as well as the addition salts with inorganic acids (hydrochlorides, hydrobromides, sulphates, nitrates, phosphates) or organic acids (succinates, fumarates, maleates, methanesulphonates, p-toluenesulphonates, isethionates).

EXAMPLES

The examples which follow, given without implied limitation, illustrate the present invention.

EXAMPLE 1

Preparation of 3-ethoxycarbonyl-6,7-difluoro-2-[N-methyl-N-(β-ethoxycarbonylethyl)amino]quinoline:

56.2 g of sodium carbonate are added to a solution of 72 g of 2-chloro-3-ethoxycarbonyl-6,7-difluoroquinoline and 45.1 g of N-methyl-N-(β-ethoxycarbonylethyl)amine in 750 cm³ of toluene. The suspension obtained is heated to approximately 90° C. and then stirred for 4 hours at this temperature. The reaction mixture is then cooled to approximately 20° C. and thereafter washed with 3 times 400 cm³ of water. The organic phase is concentrated to dryness under reduced pressure (20 kPa) at approximately 50° C. 94 g of 3-ethoxycarbonyl-6,7-difluoro-2-[N-methyl-N-(β-ethoxycarbonylethyl)amino]quinoline are obtained in the form of an oil, which is used without further purification for the subsequent steps.

Preparation of 3-ethoxycarbonyl-7,8-difluoro-1-methyl-4-oxo-1,2,3,4-tetrahydrobenzo[b][1,8]naphthyridine:

A solution of 94 g of 3-ethoxycarbonyl-6,7-difluoro-2-[N-methyl-N-(β-ethoxycarbonylethyl)amino]quinoline in 300 cm³ of absolute ethanol is added in the course of 80 minutes to a solution of 26.6 g of sodium ethylate brought to reflux in 900 cm³ of absolute ethanol. The suspension obtained, still refluxing, is stirred for a further 15 minutes. 38 cm³ of glacial acetic acid are then introduced in the course of 30 minutes. The reaction mixture is stirred for a further 15 minutes and, with the mixture still refluxing, 500 cm³ of water are then introduced in the course of 45 minutes. The suspension obtained is cooled to approximately 20° C. The precipitate is drained at approximately 20° C. and washed with twice 300 cm³ of water. The wet product is dried under reduced pressure (20 kPa) at approximately 60° C. 71.5 g of 3-ethoxy-carbonyl-7,8-difluoro-1-methyl-4-oxo-1,2,3,4-tetrahydrobenzo[b][1,8]naphthyridine are isolated in the form of a yellow solid, melting point 188° C.

Preparation of 3-ethoxycarbonyl-7,8-difluoro-1-methyl-4-oxo- 1,4-dihydrobenzo [b][1,8 ]naphthyridine:

A solution of 3.78 g of potassium iodide in 20 cm³ of water is added with stirring at approximately 20° C. to a suspension of 71 g of 3-ethoxycarbonyl-7,8-difluoro-1-methyl-4-oxo-1,2,3,4-tetrahydrobenzo[b] [1,8]naphthyridine in 1,000 cm³ of ethanol. The suspension is heated to 77° C. and 30 cm³ 33% by weight hydrogen peroxide are added in the course of 60 minutes at this temperature. The reaction mixture is kept refluxing for a further 30 minutes and is then cooled to approximately 20° C. A solution of 11.4 g of sodium thiosulphate in 50 cm³ of water is introduced in the course of 5 minutes at this temperature. The precipitate obtained is drained at approximately 20° C. and washed with twice 300 cm³ of water. The wet product obtained is dried under reduced pressure (20 kPa) at approximately 60° C. 73 g of 3-ethoxy-7,8-difluoro-1-methyl-4-oxo-1,4-dihydrobenzo[b][1,8]naphthyridine are isolated in the form of a white solid, melting point above 270° C.

2-Chloro-3-ethoxycarbonyl-6,7-difluoroquinoline may be prepared in the following manner:

50 g of 3-ethoxycarbonyl-6,7-difluorocarbostyril are added in the course of 10 minutes with stirring at 20° C. to 200 cm³ of phosphoryl chloride. The suspension is heated to a temperature in the region of 70° C. and maintained at this temperature for 3 hours. After cooling to approximately 10° C., the solution obtained is poured with stirring into a mixture of 1,000 cm³ of water and 1,000 g of crushed ice. The temperature is allowed to rise to approximately 20° C. and the mixture is extracted with twice 500 cm³ of dichloromethane. The combined organic extracts are washed with 1,000 cm³ of water, and 1,000 cm³ of water to which sodium bicarbonate has been added to pH 7, dried over sodium sulphate, filtered and concentrated to dryness under reduced pressure (20 kPa) at approximately 40° C. 45.6 g of 2-chloro-3-ethoxycarbonyl-6,7-difluoroquinoline are obtained in the form of a beige solid, melting point 108° C. which is used without further purification for the subsequent steps.

3-Ethoxycarbonyl-6,7-difluorocarbostyril may be obtained in the following manner:

62.8 g of ethyl malonate and 51 g of sodium bicarbonate are added with stirring in the course of ten minutes to a solution of 56.5 g of 3,4-difluoro-6-nitrobenzaldehyde in 92 cm³ of acetic anhydride. The suspension is maintained for 1 hour at approximately 20° C. and then heated to a temperature of approximately 75° C. for 3 hours. 400 cm³ of glacial acetic acid and then 65 cm³ of water are introduced in the course of 30 minutes at this temperature. The temperature is allowed to stabilize at approximately 50° C. and the mixture is stirred for a further 30 minutes at this temperature. 39 g of powdered iron are added portionwise in the course of 2 hours to the reaction mixture. The temperature rises to approximately 85° C. and the suspension is maintained for a further 1 hour at this temperature. The iron salts formed are drained at approximately 80° C. and then washed with twice 150 cm³ of glacial acetic acid. The filtrate and the acid washing phases are combined and treated with 700 cm³ of water. The precipitate obtained is drained at approximately 20° C. and washed with 3 times 500 cm³ of water. The wet product obtained is dried under reduced pressure (20 kPa) at approximately 50° C. 53.5 g of 3-ethoxycarbonyl-6,7-difluorocarbostyril are obtained in the form of a cream-colored solid, melting point 242° C.

3,4-Difluoro-6-nitrobenzaldehyde is prepared in the following manner:

To 520 cm³ of sulphuric acid, stirred and cooled to 0° C., 60 cm³ of fuming nitric acid are added in the course of 30 minutes. 100 g of 3,4-difluorobenzaldehyde are added in the course of 30 minutes at approximately 0° C. to the solution obtained. The temperature is allowed to rise to approximately 20° C. and the mixture is stirred for a further 3 hours at this temperature. After cooling to approximately 5° C., the reaction mixture is introduced in the course of 30 minutes with vigorous stirring into 1,200 g of crushed ice. The temperature is allowed to rise to approximately 20° C. and the mixture is extracted with twice 600 cm³ of toluene. The combined organic extracts are washed with 3 times 1,000 cm³ of water and concentrated under reduced pressure (20 kPa) to 50° C. 113 g of 3,4-difluoro-6-nitrobenzaldehyde are obtained in the form of a brown oil, which is used in the subsequent synthesis without further treatment.

EXAMPLE 2

Preparation of 3-ethoxycarbonyl-6,7-difluoro-2-[N-ethyl-N-(β -ethoxycarbonylethyl)amino]quinoline:

7.8 g of sodium carbonate are added to a solution of 10 g of 2-chloro-3-ethoxycarbonyl-6,7-difluoroquinoline and 9.7 g of N-ethyl-N-(β-ethoxycarbonylethyl)amine in 120 cm³ of toluene. The suspension obtained is heated to approximately 90° C. and then stirred for 4 hours at this temperature. The reaction mixture is then cooled to approximately 20° C. and thereafter washed with 3 times 100 cm³ of water. The organic phase is concentrated to dryness under reduced pressure (20 kPa) at approximately 50° C. 13 g of 3-ethoxycarbonyl-6,7-difluoro-2-[N-ethyl-N-(β-ethoxycarbonylethyl)amino]quinoline are obtained in the form of an oil, which is used without further purification for the subsequent step.

Preparation of 3-ethoxycarbonyl-6,7-difluoro-1-ethyl-4-oxo-1,2,3,4-tetrahydrobenzo[b][1,8]naphthyridine:

A solution of 68 g of 3-ethoxycarbonyl-6,7-difluoro-2-[N-ethyl N-(β-ethoxycarbonylethyl)amino]quinoline in 200 cm³ of absolute ethanol is introduced in the course of 60 minutes into a solution of 16.1 g of sodium ethylate brought to reflux in 600 cm³ of absolute ethanol. The suspension obtained, still refluxing, is stirred for a further 60 minutes. 20 cm³ of glacial acetic acid are then introduced in the course of 30 minutes. The reaction mixture is stirred for a further 15 minutes and, with the mixture still refluxing, 400 cm³ of water are then introduced in the course of 45 minutes. The suspension obtained is cooled to approximately 20° C. The precipitate obtained is drained at approximately 20° C. and washed with twice 200 cm³ of water. The wet product is dried under reduced pressure (20 kPa) at approximately 50° C. 52.4 g of 3-ethoxycarbonyl-7,8-difluoro-1-ethyl-4-oxo-1,2,3,4-tetrahydro-benzo[b][1,8]naphthyridine are isolated in the form of a golden-yellow solid, melting point 152° C.

Preparation of 3-ethoxycarbonyl-7,8-difluoro-1-ethyl-4-oxo- 1,4-dihydrobenzo[b][1,8]naphthyridine:

A solution of 1.7 g of potassium iodide in 10 cm³ of water is added with stirring at approximately 20° C. to a suspension of 33 g of 3-ethoxycarbonyl-7,8-difluoro-1-ethyl-4-oxo-1,2,3,4-tetrahydrobenzo[b][1,8]naphthyridine in 1,000 cm³ of ethanol. The suspension is heated to 77° C., and 12.7 cm³ of 33% by weight hydrogen peroxide are introduced in the course of 30 minutes at this temperature. The reaction mixture is kept refluxing for a further 30 minutes and is then cooled to approximately 20° C. A solution of 6 g of sodium thiosulphate in 20 cm³ of water is introduced in the course of 5 minutes at this temperature. The precipitate obtained is drained at approximately 20° C. and washed with twice 150 cm³ of water. The wet product obtained is dried under reduced pressure (20 kPa) at approximately 50° C. 28.7 g of 3-ethoxycarbonyl-7,8-difluoro-1-ethyl-4-oxo-1,4-dihydrobenzo[b][1,8]-naphthyridine are isolated in the form of a light yellow solid, melting point 270° C.

EXAMPLE 3

Preparation of 3-ethoxycarbonyl-6,7-difluoro-2-[N-cyclopropyl-N-(β-ethoxycarbonylethyl)amino]quinoline:

3 g of sodium carbonate are added to a solution of 3.48 g of 2-chloro-3-ethoxycarbonyl-6,7-difluoroquinoline and 3 g of N-cyclopropyl-N-(β-ethoxycarbonylethyl)amine in 10 cm³ of toluene. The suspension obtained is heated to reflux and then stirred for 15 hours at this temperature. The reaction mixture is then cooled to approximately 20° C. and 30 cm³ of water and 4.5 cm³ of acetic acid are thereafter added. After settling has taken place, the reaction mixture is separated and washed with twice 10 cm³ of water. The organic phase is concentrated to dryness under reduced pressure (20 kPa) at approximately 50° C. 3.3 g of crude 3-ethoxycarbonyl-6,7-difluoro-2-[N-cyclopropyl-N-(β-ethoxycarbonylethyl)amino]quinoline are obtained in the form of an oil, which is used without further purification for the subsequent step.

Preparation of 3-ethoxycarbonyl-7,8-difluoro-1-cyclopropyl-4-oxo-1,2,3,4-tetrahydrobenzo[b][1,8]naphthyridine:

A solution of 3-ethoxycarbonyl-6,7-difluoro-2-[N-cyclopropyl-N-(β-ethoxycarbonylethyl)amino]quinoline in 20 cm³ of absolute ethanol is added in the course of 60 minutes to a solution of 1.6 g of sodium ethylate brought to reflux in 40 cm³ of absolute ethanol. The solution obtained is stirred under reflux for a further 60 minutes. 2.6 cm³ of glacial acetic acid are then introduced in the course of 10 minutes. The reaction mixture is stirred for a further 15 minutes and, with the mixture still refluxing, 26 cm³ of water are then introduced in the course of 5 minutes. The suspension obtained is cooled to approximately 20° C. The precipitate is drained at approximately 20° C. and washed with twice 10 cm³ of water. The wet product is dried under reduced pressure (20 kPa) at approximately 60° C. 1.25 g of crude 3-ethoxycarbonyl-7,8-difluoro-1-cyclopropyl-4-oxo-1,2,3,4-tetrahydrobenzo[b][1,8]naphthyridine are isolated in the form of a yellow solid, melting point 172° C.

Preparation of 3-ethoxycarbonyl-7,8-difluoro-1-cyclopropyl-4-oxo-1,4-dihydrobenzo[b][1,8]naphthyridine:

A solution of 0.053 g of potassium iodide in 0.5 cm³ of water is added with stirring at approximately 20° C. to a suspension of 1 g of 3-ethoxycarbonyl-7,8-difluoro-1-cyclopropyl-4-oxo-1,2,3,4-tetrahydrobenzo[b][1,8]naphthyridine in 14 cm³ of ethanol. The suspension is heated to 77° C., and 0.5 cm³ of 33% by weight hydrogen peroxide are introduced in the course of 5 minutes at this temperature. The reaction mixture is kept refluxing for a further 60 minutes and then cooled to approximately 20° C. 1.06 cm³ of 1N sodium thiosulphate solution are introduced in the course of 5 minutes at this temperature. The precipitate obtained is drained at approximately 20° C. and washed with twice 10 cm³ of water. The wet product obtained is dried under reduced pressure (20 kPa) at approximately 60° C. 0.7 g of crude 3-ethoxycarbonyl-7,8-difluoro-1-cyclopropyl-4-oxo-1-dihydrobenzo[b][1,8]naphthyridine is isolated in the form of an ochre-white solid, melting point 210° C.

EXAMPLE 4

3-Ethoxycarbonyl-6,7-difluoro-2-[N-methyl-N-(β-cyanoethyl)amino]quinoline is prepared in the following manner:

19.08 g of sodium carbonate are added to a solution of 16.3 g of 2-chloro-3-ethoxycarbonyl-6,7-difluoroquinoline and 10 g of N-methyl-N-(β-cyanoethyl)amine in 160 cm³ of toluene. The suspension obtained is heated to reflux and then stirred for 4 hours at this temperature. The reaction mixture is then cooled to approximately 20° C. and thereafter washed with 3 times 50 cm³ of water. The organic phase is concentrated to dryness under reduced pressure (20 kPa) at approximately 50° C. 19.17 g of 3-ethoxycarbonyl-6,7-difluoro-2-[N-methyl-N-(β-cyanoethyl)amino]quinoline are obtained in the form of an oil, which is used without further purification for the subsequent steps.

3-Cyano-7,8-difluoro-1-methyl-4-oxo-1,2,3,4-tetrahydrobenzo[b][1,8]naphthyridine is prepared in the following manner:

A solution of 19.17 g of 3-ethoxycarbonyl-6,7-difluoro-2-[N-methyl-N-(β-cyanoethyl)amino]quinoline in 50 cm³ of tetrahydrofuran is introduced in the course of 60 minutes into a solution, cooled to −10° C., of 8.74 g of potassium tert-butylate in 200 cm3 of tetrahydrofuran. The suspension obtained is stirred, still at −10° C., for a further 30 minutes. 4 cm³ of glacial acetic acid are then introduced. The tetrahydrofuran is evaporated off under reduced pressure (20 kPa). The crude reaction mixture is taken up with 200 cm³ of an aqueous-alcoholic ethanol/water (70/30 vol/vol) mixture. The precipitate obtained is filtered off, washed with twice 50 cm³ of water and then dried under reduced pressure (20 kPa). 16.1 g of 3-cyano-7,8-difluoro-1-methyl-4-oxo-1,2,3,4tetrahydrobenzo[b][1,8]naphthyridine are isolated in the form of a golden-yellow solid, melting point 144° C.

3-Cyano-7,8-difluoro-1-methyl-4-oxo-1,4-dihydrobenzo[b][1,8]naphthyridine is prepared in the following manner:

A solution of 0.47 g of potassium iodide in 5 cm³ of water is added with stirring at approximately 20° C. to a suspension of 8.6 g of 3-cyano-7,8-difluoro-1-methyl-4-oxo-1,2,3,4-tetrahydrobenzo[b][1,8]naphthyridinein 350 cm³ of ethanol. The suspension is heated to 77° C., and 4 cm³ of 33% by weight hydrogen peroxide are added in the course of 10 minutes at this temperature. The reaction mixture is kept refluxing for a further 30 minutes and is then cooled to approximately 20° C. 10 cm³ of 1N sodium thiosulphate solution are added in the course of 5 minutes at this temperature. The precipitate obtained is drained at approximately 20° C. and washed with twice 20 cm³ of water. The wet product obtained is dried under reduced pressure (20 kPa) at approximately 50° C. 8 g of 3-cyano-7,8-difluoro-1-methyl-4-oxo-1,4dihydrobenzo[b][1,8]naphthyridine are obtained in the form of a light yellow solid, melting point 380° C.

EXAMPLE 5

3-Ethoxycarbonyl-6,7-difluoro-2-{N-methyl-N-(-(N'N'-dimethylaminocarbonyl)ethyl]amino}quinoline is prepared in the following manner:

31 g of sodium carbonate are added to a solution of 26 g of 2-chloro-3-ethoxycarbonyl-6,7-difluoroquinoline and 25 g of N-methyl-N-[β-(N',N'-dimethylaminocarbonyl)ethyl]amine in 300 cm³ of toluene. The suspension obtained is heated to reflux and then stirred for 2 hours 30 minutes at this temperature. The reaction mixture is then cooled to approximately 20° C. and thereafter washed with 3 times 100 cm³ of water. The organic phase is concentrated to dryness under reduced pressure (20 kPa) at approximately 50° C. 35 g of 3-ethoxycarbonyl-6,7-difluoro-2-{N-methyl-N(β-(N',N' -dimethylaminocarbonyl)ethyl]amino}quinoline are obtained in the form of an oil, which is used without further purification for the subsequent steps.

N-N-Dimethyl-7,8-difluoro-1-methyl-4-oxo-1,2,3,4tetrahydrobenzo[b][1,8]naphthyridine-3-carboxamide is prepared in the following manner:

A solution of 35 g of 3-ethoxycarbonyl-6,7 -difluoro-2-{N-methyl-N-[β-(N',N'-dimethylaminocarbonyl)ethyl]amino}quinoline in 150 cm³ of tetrahydrofuran is added in the course of 75 minutes to a solution of 15.7 g of potassium tert-butylate in 150 cm³ of tetrahydrofuran cooled to 0° C. The suspension obtained is then stirred at 0° C. for a further 30 minutes and 8 cm³ of glacial acetic acid are thereafter added. The tetrahydrofuran is evaporated off under reduced pressure (20 kPa). The crude reaction mixture is taken up with 200 cm³ of an aqueous-alcoholic ethanol/water (70:30 vol/vol) mixture. The precipitate obtained is filtered off, washed 3 times with 100 cm³ of water and then dried under vacuum (20 kPa). 25 g of N,N-dimethyl-7,8-difluoro-1-methyl-4-oxo-1,2,3,4tetrahydrobenzo[b][1,8]naphthyridine-3-carboxamide are isolated in the form of a lemon-yellow solid, melting point 206° C.

N,N-Dimethyl-7,8-difluoro-1-methyl-4-oxo-1,4-dihydrobenzo[b][1,8]naphthyridine-3-carboxamide is prepared in the following manner:

A solution of 1.35 g of potassium iodide in 10 cm³ of water is added with stirring at approximately 20° C. to a suspension of 25 g of N,N-dimethyl-7,8 -difluoro-1-methyl-4-oxo-1,2,3,4-tetrahydrobenzo[b][1,8]naphthyridine-3-carboxamide in 1,000 cm³ of ethanol. The suspension is heated to 77° C., and 25 cm³ of 33% by weight hydrogen peroxide are introduced in the course of 20 minutes at this temperature. The reaction mixture is kept refluxing for a further 1 hour 30 minutes and is then cooled to approximately 20° C. 30 cm³ of 1N sodium thiosulphate solution are introduced in the course of 5 minutes at this temperature. The precipitate obtained is drained at approximately 20° C. and washed with twice 60 cm³ off water. The wet product obtained is dried under reduced pressure (20 kPa) at approximately 50° C. 19.5 g of N,N-dimethyl-7,8 -difluoro-1-methyl-4-oxo-1,4-dihydrobenzo[b][1,8] naphthyridine-3-carboxamide are isolated in the form of a light yellow solid, melting point 324° C.

EXAMPLE 6

3-Ethoxycarbonyl-6,7-difluoro-2-[N-methyl-N-(β-aminocarbonylethyl)amino]quinoline is prepared in the following manner:

4.4 g of sodium carbonate are added to a solution of 4 g of 2-chloro-3-ethoxycarbonyl-6,7-difluoroquinoline and 3 g of N-methyl-N-(β-aminocarbonylethyl)amine in 40 cm³ of toluene. The suspension obtained is heated to reflux and then stirred for 2 hours 30 minutes at this temperature. The reaction mixture is then cooled to approximately 20° C. and thereafter washed with 3 times 25 cm³ of water. The organic phase is concentrated to dryness under reduced pressure (20 kPa) at approximately 50° C. 4.7 g of 3-ethoxycarbonyl-6,7-difluoro-2-[N-methyl-N-(β-aminocarbonylethyl)amino]quinoline are obtained in the form of an oil, which is used without further purification for the subsequent steps.

3-Carboxamide-7,8-difluoro-1-methyl-4-oxo-1,2,3,4tetrahydrobenzo[b][1,8]naphthyridine is prepared in the following manner:

A solution of 4.23 g of 6,7-difluoro-2-[N -methyl-N-(β-aminocarbonylethyl)amino]quinoline in 20 cm³ of tetrahydrofuran is added in the course of 30 minutes to a solution of 1.8 g of potassium tert-butylate in 50 cm³ of tetrahydrofuran cooled to 0° C. The suspension obtained is then stirred at [lacuna]°C. for a further 30 minutes and thereafter 2 cm³ of glacial acetic acid are introduced. The tetrahydrofuran is evaporated off under reduced pressure (20 kPa). The crude reaction mixture is taken up with 10 cm³ of an aqueous-alcoholic ethanol/water (70:30 vol/vol) mixture. The precipitate obtained is filtered off, washed 3 times with 10 cm³ of water and then dried under reduced pressure (20 kPa). 1.6 g of 3-carboxamide-7,8-difluoro-1-methyl-4-oxo-1,2,3,4-tetrahydrobenzo[b][1,8]naphthyridine are obtained in the form of a yellow solid, melting point 182° C.

3-Carboxamide-7,8-difluoro-1-methyl-4-oxo-1,4dihydrobenzo[b][1,8]naphthyridine is prepared in the following manner:

A solution of 0.1 g of potassium iodide in 1 cm³ of water is added with stirring at approximately 20° C. to a suspension of 1.3 g of 3-carboxamide-7,8 -difluoro-1-methyl-4-oxo-1,2,3,4-tetrahydrobenzo[b][1,8]naphthyridine in 25 cm³ of ethanol. The suspension is heated to 77° C., and 1.5 cm³ of 33% by weight hydrogen peroxide are added in the course of 5 minutes at this temperature. The reaction mixture is kept refluxing for a further 1 hour 30 minutes and is then cooled to approximately 20° C. 1 cm³ of 1N sodium thiosulphate solution is added at this temperature. The precipitate obtained is drained at approximately 20° C. and washed with twice 5 cm³ of water. The wet product obtained is dried under reduced pressure (20 kPa) at approximately 50° C. 1.1 g of 3-carboxamide-7,8 -difluoro-1-methyl-4-oxo-1,4-dihydrobenzo[b][1,8]naphthyridine are isolated in the form of an orange-colored solid, melting point 318° C.

EXAMPLE 7

Using the procedure described above in Example 5, the following products are prepared:

N,N-dimethyl-7,8-difluoro-1-ethyl-4-oxo-1,4-dihydrobenzo[b][1,8]naphthyridine-3-carboxamide;

N,N-dimethyl-7,8-difluoro-1-cyclopropyl-4-oxo-1,4-dihydrobenzo[b][1,8]naphthyridine-3-carboxamide;

N,N-diethyl-7,8-difluoro-1-methyl-4-oxo-1,4-dihydrobenzo[b][1,8]naphthyridine-3-carboxamide;

N,N-diethyl-7,8-difluoro-1-ethyl-4-oxo-1,4-dihydrobenzo[b][1,8]naphthyridine-3-carboxamide;

N,N-diethyl-7,8-difluoro-1-cyclopropyl-4-oxo-1,4-dihydrobenzo[b][1,8]naphthyridine-3-carboxamide;

1-(7,8-difluoro-1-methyl-4-oxo-1,4-dihydrobenzo[b][1,8]naphthyridine-3-carbonyl)pyrrolidine;

1-(7,8-difluoro-1-ethyl-4-oxo-1,4-dihydrobenzo[b][1,8]naphthyridine-3-carbonyl)pyrrolidine;

1-(7,8-difluoro-1-cyclopropyl-4-oxo-1,4-dihydrobenzo[b][1,8]naphthyridine-3-carbonyl)pyrrolidine;

1-(7,8-difluoro-1-methyl-4-oxo- 1,4-dihydrobenzo[b][1,8]naphthyridine-3-carbonyl)piperidine;

1-(7,8-difluoro-1-ethyl-4-oxo-1,4-dihydrobenzo[b][1,8]naphthyridine-3-carbonyl)piperidine;

1-(7,8-difluoro-1-cyclopropyl-4-oxo-1,4-dihydrobenzo[b][1,8]naphthyridine-3-carbonyl)piperidine;

1-(7,8-difluoro-1-methyl-4-oxo-1,4-dihydrobenzo[b][1,8]naphthyridine-3-carbonyl)morpholine;

1-(7,8-difluoro-1-ethyl-4-oxo-1,4-dihydrobenzo[b][1,8]naphthyridine-3-carbonyl)morpholine;

1-(7,8-difluoro-1-cyclopropyl-4-oxo-1,4-dihydrobenzo[b] [1,8]naphthyridine-3-carbonyl)morpholine;
1-(7,8-difluoro-1-methyl-4-oxo- 1,4-dihydrobenzo[b][1,8] naphthyridine-3-carbonyl)thiomorpholine;
1-(7,8-difluoro-1-ethyl-4-oxo-1,4-dihydrobenzo[b][1,8] naphthyridine-3-carbonyl)thiomorpholine;
1-(7,8-difluoro-1-cyclopropyl-4-oxo-1,4-dihydrobenzo[b][1,8]naphthyridine-3-carbonyl)thiomorpholine;
1-(7,8-difluoro-1-methyl-4-oxo- 1,4-dihydrobenzo[b][1,8] naphthyridine-3-carbonyl)-4-methylpiperazine;
1-(7,8-difluoro-1-ethyl-4-oxo-1,4-dihydrobenzo[b][1,8] naphthyridine-3-carbonyl)-4-methylpiperazine;
1-(7,8-difluoro-1-cyclopropyl-4-oxo-1,4-dihydrobenzo[b] [1,8]naphthyridine-3-carbonyl)-4methylpiperazine.

The products of general formula (I) obtained in the above examples may be used as described below:

Application Example 1

3-Cyano-7-fluoro-1-methyl-8-(4-methyl-1 -piperazinyl)-4-oxo-1,4-dihydrobenzo[b][1,8]naphthyridine is prepared in the following manner:

A suspension of 2.1 g of 3-cyano-7,8 -difluoro-1-methyl-4-oxo-1,4-dihydrobenzo[b][1,8]naphthyridine in 100 cm$^3$ of dimethyl sulphoxide is heated to 80° C. in the presence of 2 cm$^3$ of N-methylpiperazine. The reaction mixture is maintained at this temperature for 8 hours. The solution obtained is cooled to room temperature and stirred at this temperature for 15 hours. The precipitate formed is filtered off, washed with 3 times 20 cm$^3$ of water and dried under vacuum (20 kPa) at 50° C. 2.6 g of 3-cyano-7-fluoro-1-methyl-8-(4-methyl-1-piperazinyl)-4oxobenzo[b][1,8]naphthyridine are obtained in the form of a yellow precipitate, melting point 335° C.

7-Fluoro-1-methyl-8-(4-methyl-1-piperazinyl) -4-oxo-1,4-dihydrobenzo[b][1,8]naphthyridine-3carboxylic acid is prepared in the following manner:

A suspension of 2 g of 3-cyano-7-fluoro-1 -methyl-8-(4-methyl-1-piperazinyl)-4-oxo-1,4-dihydrobenzo[b][1,8] naphthyridine is heated to reflux in 40 cm$^3$ of 12N hydrochloric acid. The reaction mixture is maintained at this temperature for 15 hours. The solution obtained is cooled to room temperature. The product which crystallizes is filtered off, washed with water to neutrality and dried under reduced pressure (20 kPa) at 50° C. 1.5 g of 7-fluoro-1-methyl-8-(4 -methyl-1-piperazinyl)-4-oxo-1,4-dihydrobenzo[b][1,8] naphthyridine-3-carboxylic acid monohydrochloride are obtained in the form of yellow crystals, melting point 290° C. (decomposition).

Application Example 2

A suspension of 2.96 g of 7,8-difluoro-N,N-dimethyl-4-oxo-1-methyl-1,4-dihydrobenzo[b][1,8] naphthyridine-3-carboxamide, 1.12 g of 1-methylpiperazine and 1.55 g of potassium carbonate in 100 cm$^3$ of dimethyl sulphoxide is heated with stirring for 5 hours at approximately 80° C. After cooling to approximately 20° C., the reaction mixture is treated with 100 cm$^3$ of water; the insoluble matter is drained and washed with twice 30 cm$^3$ of water and twice 30 cmof ethanol.

2.3 g of N,N-dimethyl-7-fluoro-1-methyl-8-(4 -methyl-1-piperazinyl)-4-oxo-1,4-dihydrobenzo-[b][1,8] -naphthyridine-3-carboxamide are obtained in the form of a yellow solid, which decomposes at 275° C.

A solution of 0.5 g of N,N-dimethyl-7-fluoro-1-methyl-8-(4-methyl-1-piperazinyl)-4-oxo-1,4-dihydrobenzo[b][1,S] naphthyridine-3-carboxamide in 10 cm$^3$ of 6N aqueous hydrochloric acid is heated with stirring to approximately 95° C. for 5 hours. After cooling to approximately 20° C. the insoluble matter is drained and washed with 3 times 20 cm$^3$ of water and twice 10 cm$^3$ of ethanol.

The product obtained is suspended in 30 cm$^3$ of water; 0.6 cm$^3$ of N aqueous potassium hydroxide is added and the mixture is stirred for 1 hour at approximately 20° C. The insoluble matter is drained and washed with twice 20 cm$^3$ of water and twice 10 cm$^3$ of ethanol. After recrystallisation in 15 cm$^3$ of dimethylformamide, 0.15 g of 7-fluoro-1-methyl-8-(4-methyl-1-piperazinyl)-4-oxo-1,4-dihydrobenzo[b][1,8] naphthyridine-3-carboxylic acid is obtained in the form of a yellow solid, which decomposes at 354° C.

Application Example 3

A suspension of 1.3 g of 7,8-difluoro-1 -methyl-4-oxo-1,4-dihydrobenzo[b][1,8]naphthyridine-3carboxamide, 0.54 g of 1-methylpiperazine and 0.75 g of potassium carbonate in 25 cm$^3$ of dimethyl sulphoxide is heated to approximately 80° C. for 6 hours. After cooling to a temperature in the region of 20° C., the reaction mixture is treated with 100 cm$^3$ of water. The insoluble matter is drained and washed with twice 20 cm$^3$ of water and twice 20 cm$^3$ of ethanol.

The product obtained is chromatographed on 20 g of silica gel (0.063–0.200 mm) suspended in a dichloromethane mixture containing 10% of methanol. Reaction impurities are removed by elution with 500 cm3 of this solvent mixture. The expected product is then eluted with 500 cm$^3$ of the same solvent mixture. After concentration to dryness under reduced pressure (20 kPa) at approximately 40° C. the solid residue is recrystallised in 25 cm$^3$ of dimethylformamide, drained and washed with twice 30 cm$^3$ of ethanol at approximately 70° C.

0.6 g of 7-fluoro-1-methyl-8-(4-methyl-1 -piperazine)-4-oxo-1,4-dihydrobenzo[b][1,8] naphthyridine-3-carboxamide is obtained in the form of a yellow solid, which decomposes at 265° C.

7-Fluoro-8-(4-methyl-1-piperazinyl)-1-methyl-4-oxo-1, 4-dihydrobenzo[b][1,8]naphthyridine-3carboxylic acid is prepared under the conditions of Application Example 2, but starting with 0.3 g of 7-fluoro-1-methyl-1-8-(4-methyl-1-piperazinyl)-4-oxo-1,4-dihydrobenzo[b][1,8]naphthyridine-3-carboxamide. After cooling to approximately 20° C., the reaction mixture is treated with 50 cm$^3$ of water; the insoluble matter is drained and washed with twice 10 cm$^3$ of water.

The product obtained is suspended in 20 cm$^3$ of water, treated with 0.4 cm$^3$ of N aqueous potassium hydroxide solution and stirred for 1 hour at approximately 20° C. The insoluble matter is drained, washed with 3 times 10 cm$^3$ of water and twice 10 cm$^3$ of ethanol and recrystallized in 20 cm$^3$ of dimethylformamide.

0.17 g of 7-fluoro-1-methyl-8-(4-methylpiperazinyl)-1,4-dihydrobenzo[b][1,8]naphthyridine-3carboxylic acid is obtained in the form of a yellow solid, which decomposes at 354° C.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:
1. A process for preparing benzo[b]naphthyridines of the formula:

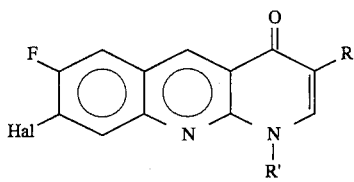

in which R is a carboxyl, alkyloxycarbonyl, cyano, carbamoyl, alkylcarbamoyl, benzylcarbamoyl or hydroxyethylcarbamoyl radical or a dialkylaminoethylcarbamoyl or dialkylcarbamoyl radical in which the alkyl portions, with the nitrogen atom to which they are attached, optionally form a 5- or 6-membered heterocycle optionally containing another hetero atom selected from oxygen, sulphur and nitrogen and optionally substituted on the nitrogen with an alkyl radical, R' is selected from a hydrogen atom or an alkyl, fluoroalkyl, carboxylalkyl, cycloalkyl (containing 3 to 6 carbon atoms), fluorophenyl, difluorophenyl, alkyloxy or alkylamino radical and Hal is a halogen atom, as well as their salts where they exist, comprising the following operations being performed:
1) condensation of an amine of formula:

in a basic medium, in an organic solvent, in which R' is defined as before and R" is selected from an alkyloxycarbonyl, cyano, carbamoyl, alkylcarbamoyl, benzylcarbamoyl or hydroxyethylcarbamoyl radical or a dialkyaminoethylcarbamoyl or dialkylcarbamoyl radical in which the alkyl portions, with the nitrogen atom to which they are attached, optionally form a 5- or 6-membered heterocycle optionally containing another hetero atom selected from oxygen, sulphur and nitrogen and optionally substituted on the nitrogen with an alkyl radical, with a chlorofluoroquinoline of formula:

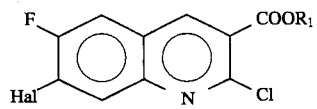

in which Hal is defined as above and $R_1$ is a hydrogen atom or an alkyl radical, the alkyl radicals mentioned above are unbranched or branched and contain 1 to 4 carbon atoms,
2) cyclization of the fluoroquinoline thereby obtained in a basic medium, of formula:

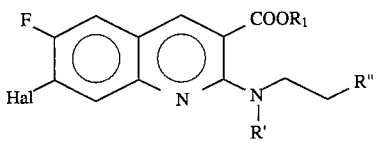

in which R', R" and Hal are defined as before and $R_1$ is defined as above in 1),
3) oxidation of the 1,2,3,4-tetrahydro-benzo[b][1,8]naphthyridine of formula:

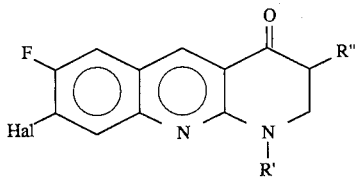

with hydrogen peroxide, in which Hal, R' and R" are defined as before, and then, optionally, conversion of the ester obtained for which R is alkyl to an acid for which R is a hydrogen atom, and optionally, conversion of the acid obtained to a salt.

2. A benzonaphthyridine derivative of the formula:

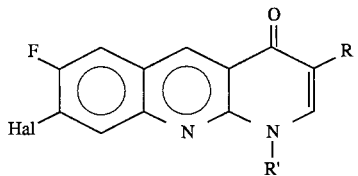

in which R' selected from a hydrogen atom, alkyl, fluoroalkyl, carboxyalkyl, cycloalkyl having 3 to 6 carbon atoms, fluorophenyl, difluorophenyl, alkoxy or an alkylamino radical and Hal is a halogen atom and R is selected from a cyano, carbamoyl, alkylcarbamoyl, benzylcarbamoyl or hydroxyethylcarbamoyl radical or a dialkylaminoethylcarbamoyl or dialkylcarbamoyl radical in which the alkyl portions, with the nitrogen atom to which they are attached, can optionally form a 5- or 6-membered heterocycle optionally containing another hereto atom selected from oxygen, sulphur and nitrogen and optionally substituted on the nitrogen with an alkyl radical.

* * * * *

UNITED STATES PATENT AND TRADEMARK OFFICE
CERTIFICATE OF CORRECTION

PATENT NO. : 5,484,921
DATED : January 16, 1996
INVENTOR(S) : Christophe Daubie and Jean-Jacques Legrand It is certified that error appears in the above-indentified patent and that said Letters Patent is hereby corrected as shown below:

Title page, col. 2, in the Abstract, 9th line of text, second line below formula (IV), insert a space between "4" and "benzo".

Signed and Sealed this

Fourteenth Day of May, 1996

Attest:

BRUCE LEHMAN

*Attesting Officer*      *Commissioner of Patents and Trademarks*